(12) United States Patent
Shohmi et al.

(10) Patent No.: US 8,354,078 B2
(45) Date of Patent: Jan. 15, 2013

(54) LIQUID ASPIRATING TUBE, LIQUID DISPENSING APPARATUS AND LIQUID DISPENSING METHOD

(75) Inventors: Keiichiro Shohmi, Kobe (JP); Tomoyuki Nishida, Ashiya (JP); Yoshinori Ooi, Kobe (JP)

(73) Assignee: Sysmex Corporation, Kobe (JP)

( * ) Notice: Subject to any disclaimer, the term of this patent is extended or adjusted under 35 U.S.C. 154(b) by 36 days.

(21) Appl. No.: 12/079,788

(22) Filed: Mar. 28, 2008

(65) Prior Publication Data

US 2008/0240994 A1 Oct. 2, 2008

(30) Foreign Application Priority Data

Mar. 30, 2007 (JP) ................... 2007-094429
Mar. 30, 2007 (JP) ................... 2007-094563

(51) Int. Cl.
| | |
|---|---|
| *G01N 21/00* | (2006.01) |
| *G01N 31/00* | (2006.01) |
| *G01N 33/00* | (2006.01) |
| *G01N 35/00* | (2006.01) |
| *G01N 35/02* | (2006.01) |
| *B01L 3/02* | (2006.01) |

(52) U.S. Cl. .......... 422/511; 422/63; 422/509; 422/510; 436/43; 436/49

(58) Field of Classification Search ............ 422/100, 422/510–511; 436/49
See application file for complete search history.

(56) References Cited

U.S. PATENT DOCUMENTS

| | | | |
|---|---|---|---|
| 3,913,577 A * | 10/1975 | Nehra et al. ............... 604/268 |
| 5,428,993 A | 7/1995 | Kobashi | |
| 6,267,927 B1 * | 7/2001 | Pomar Longedo et al. ..... 422/65 |
| 6,495,106 B1 * | 12/2002 | Kalra et al. ................... 422/510 |
| 6,691,748 B1 * | 2/2004 | Tajima ........................ 422/100 |
| 7,171,863 B2 * | 2/2007 | Tamura et al. .............. 73/864.14 |
| 2002/0031837 A1 * | 3/2002 | Matsubara et al. ........... 422/68.1 |
| 2002/0051737 A1 * | 5/2002 | Sollbohmer et al. .......... 422/100 |
| 2005/0013744 A1 * | 1/2005 | Nagai et al. ................. 422/100 |

FOREIGN PATENT DOCUMENTS

| | | |
|---|---|---|
| JP | 62-184359 A | 8/1987 |
| JP | 62-184361 A | 8/1987 |
| JP | 05-084864 U | 11/1993 |
| JP | 06-003364 | 1/1994 |

(Continued)

OTHER PUBLICATIONS

International Search Report for International Application No. PCT/JP2010/054490, dated May 18, 2010, 2 pages.

*Primary Examiner* — Jill Warden
*Assistant Examiner* — Charles D Hammond
(74) *Attorney, Agent, or Firm* — Brinks Hofer Gilson & Lione

(57) ABSTRACT

The present invention is to present a liquid dispensing apparatus which is capable of preventing contamination by previously aspirated liquid, even when residual liquid in a pipette tip separated from the dispensing apparatus is scattered. The liquid dispensing apparatus includes: sample dispensing arm 5 which comprises a dispensing nozzle 54*b* for aspirating and discharging sample on which a pipette tip 200 is attached; tip separating section 140 for separating the pipette tip 200 from the dispensing nozzle 54*b*; and nozzle wiping section 16 for cleaning a tip of the dispensing nozzle 54*b*.

10 Claims, 15 Drawing Sheets

FOREIGN PATENT DOCUMENTS

| | | |
|---|---|---|
| JP | 2531074 Y2 | 4/1997 |
| JP | 10-002902 A | 1/1998 |
| JP | 11-248714 | 9/1999 |
| JP | 2003-066049 A | 3/2003 |
| JP | 2003-315351 A | 11/2003 |
| JP | 2008-249659 A | 10/2008 |
| WO | WO 2007/047069 A2 | 4/2007 |

* cited by examiner

LIQUID ASPIRATING TUBE, LIQUID DISPENSING APPARATUS AND LIQUID DISPENSING METHOD

RELATED APPLICATIONS

This application claims priority under 35 U.S.C. §119 to Japanese Patent Application No. 2007-094429 filed Mar. 30, 2007 and Japanese Patent Application No. 2007-094563 filed Mar. 30, 2007, the entire contents of which are hereby incorporated by reference.

FIELD OF THE INVENTION

The present invention relates to a liquid aspirating tube, a liquid dispensing apparatus and liquid dispensing method for aspirating liquid such as sample, reagent and the like by using a pipette tip.

BACKGROUND

In analyzers which have a dispensing nozzle for aspirating and discharging liquid such a blood sample, reagent and the like, it is important to prevent contamination by a previously aspirated liquid in order to ensure the accuracy of the analysis when another new liquid is aspirated after the previously aspirated liquid was discharged. Therefore, for example, Japanese Laid-Open Patent Publication No. H6-3364 discloses a dispensing device in which a disposable pipette tip is installed on the tip of a dispensing nozzle, and after use the disposable pipette tip is removed and replaced by a new pipette tip.

The dispensing device disclosed in Japanese Laid-Open Patent Publication No. H6-3364 separates the pipette tip from the dispensing nozzle through impacting the top surface of the pipette tip on a releasing plate by inserting the dispensing nozzle, which has installed the pipette tip, into the notched part of the releasing plate and thereafter moving up the dispensing nozzle.

However, in the art disclosed in Japanese Laid-Open Patent Publication No. H6-3364, liquid that remains in the pipette tip is sometimes scattered when the pipette tip is separated by impacting the top surface of the pipette tip on the releasing plate, and the scattered liquid may adhere to the tip of the dispensing nozzle. In this case, the liquid may also adhere to the aspirating hole provided in the tip of the dispensing nozzle. When residual liquid in the pipette tip adheres to the tip of the dispensing nozzle, the liquid used in a subsequent analysis may be contaminated even though the pipette tip is replaced, thereby the accuracy of the analysis may be impaired.

In order to solve this problem, the dispensing device disclosed in Japanese Laid-Open Patent Publication No. 11-248714 looses the connection between the pipette tip and the nozzle part by lowering the nozzle part so as to bring the tapered part of the pipette tip into contact with an pressing plate which is located at a position slightly distanced from the center axis of the nozzle part and applying a pressing force in a horizontal direction on the pipette tip by the pressing plate, when separating the pipette tip from the nozzle base. Thereafter, the pipette tip is smoothly separated from the nozzle part by moving up the nozzle part and impacting the top surface of the pipette tip on an ejection plate.

In recent years, there has been a trend to reduce the quantity of samples such as blood collected from a patient to minimize the burden on the patient, and there has likewise been a demand for analyzers to reduce the amount of sample required for analysis. A further desire for high performance analyzers has arisen in conjunction with the increasing number of samples to be measured by the analyzers.

It is necessary to improve capability of the dispensing apparatus to dispense minute amount of sample in order to perform high accuracy analysis with a reduced amount of sample. Therefore a long and narrow pipette tip has been used recently. When such a long and narrow pipette tip is used and the pipette tip is separated from the dispensing nozzle, the angle formed by the tapered part of the pipette tip at the leading end and the perpendicular axis becomes extremely narrow. When the art disclosed in Japanese Laid-Open patent Publication No. 11-248714 is applied to the dispensing device using this type of pipette tip, problems arises such as (1) the position of the leading end of the descending pipette tip and the position of the pressing plate must be set in proximity in order to apply a horizontal force to the pipette tip by the pressing plate in conjunction with the descent of the pipette tip, because due to the narrow angle of the tapered part of the pipette tip. Therefore, high precision components and precision assembly are demanded for the pressing plate, and high precision control is demanded when lowering the nozzle on which the pipette tip is installed, (2) the horizontal force applied to the descending pipette tip by the pressing plate becomes weak due to the narrow angle of the tapered part of the pipette tip, and the residual liquid is scattered when the top surface of the pipette tip impacts on the ejection plate, and (3) causing problems (1) and (2) in conjunction with speeding up of the dispensing device.

BRIEF SUMMARY

A first aspect of the present invention is a liquid dispensing apparatus, comprising: a dispenser which comprises a dispensing nozzle for aspirating and discharging liquid on which a pipette tip is attached; a separating section for separating the pipette tip from the dispensing nozzle; and a nozzle cleaning section for cleaning a tip of the dispensing nozzle.

A second aspect of the present invention is a liquid dispensing method, comprising steps of: attaching a pipette tip on a dispensing nozzle; aspirating liquid contained in a liquid container into the pipette tip attached on the dispensing nozzle; discharging the aspirated liquid into a target container; separating the pipette tip from the dispensing nozzle; and cleaning a tip of the dispensing nozzle.

A third aspect of the present invention is a liquid aspirating tube for aspirating liquid on which a pipette tip is attached, comprising an aspirating hole section having an aspirating hole for aspirating the liquid into the pipette tip, near a tip of the liquid aspirating tube, the aspirating hole being open laterally.

DETAILED DESCRIPTION OF THE PREFERRED EMBODIMENTS

Figure 1:
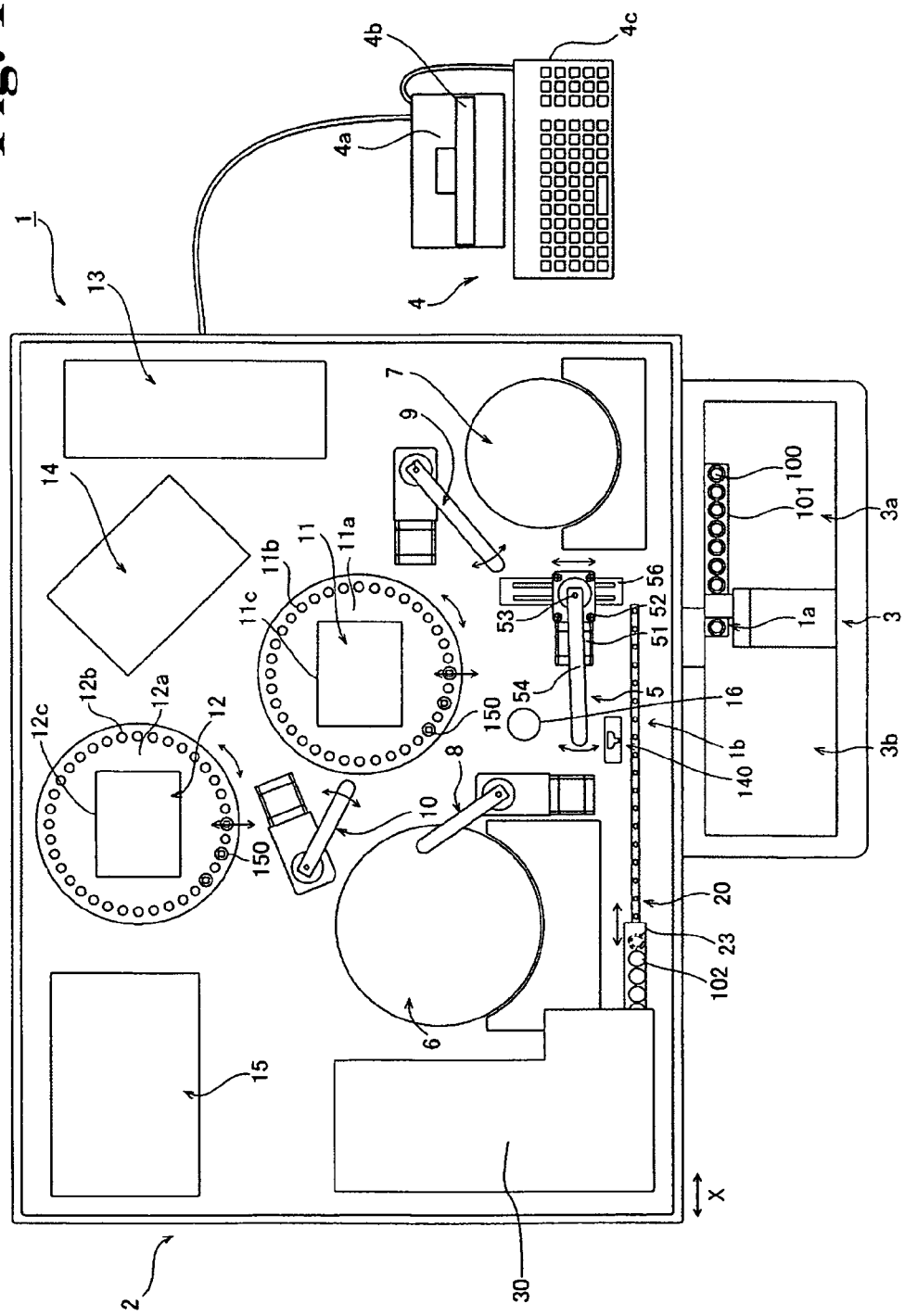
FIG. 1 is a plan view of an immunoanalyzer of an embodiment of the present invention.

The preferred embodiments of the present invention are described hereinafter based on the drawings.

The overall structure of the immunoanalyzer 1 of an embodiment of the present invention is described below with reference to FIGS. 1 and 2.

The immunoanalyzer 1 of the present embodiment of the invention performs examinations using samples such as blood for various items such as hepatitis B, hepatitis C, tumor markers, thyroid hormone and the like. The immunoanalyzer 1 removes an R1 reagent, which includes free capture antibodies, by attracting bound reagent, capture reagent, and magnetic particles to a magnet (not shown in the drawings) of the BF (Bound Free) separator 14 (refer to FIGS. 1 and 2) after magnetic particles (R2 reagent) have been bound to capture antibodies (R1 reagent) bonded to the antigen contained in a measurement object sample such as blood or the like. Then, after the antigen with bound magnetic particles has bonded with a labeling antibody (R3 reagent), the R3 reagent which includes the free labeling antibody is removed by attracting the bound magnetic particles, antigen, and labeling antibody to the magnet of the BF separator 14. After a luminous substrate which emits light (R5 reagent) has been added in the labeling antibody reaction process, the amount of light emission generated by the reaction of the luminous substrate and the labeling antibody is measured. The antibody or antigen contained in the sample with the bonded labeling antibody can be quantitatively measured through this process.

Figure 2:
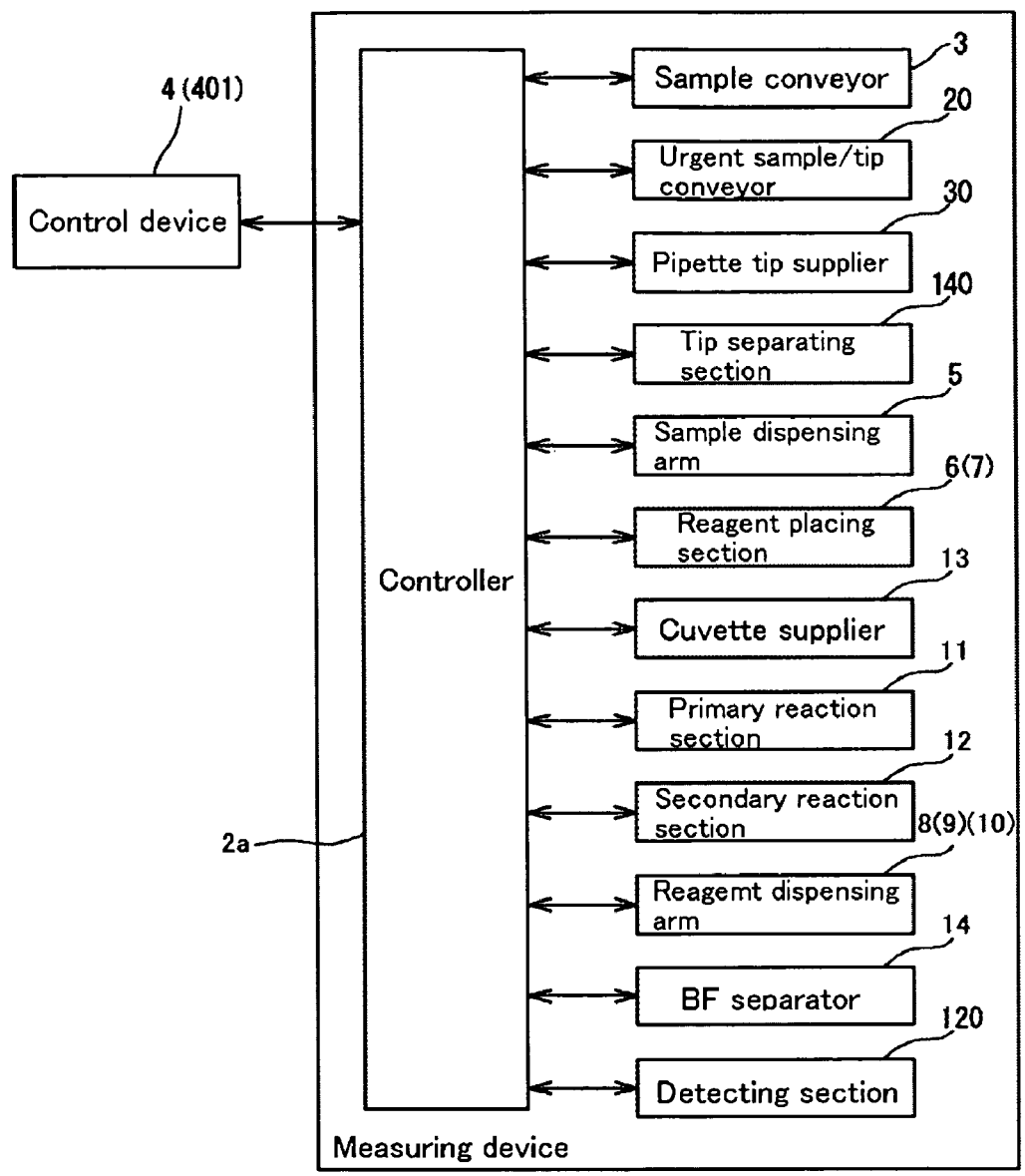
FIG. 2 is a block diagram which includes the control section of the measuring device of the immunoanalyzer of the embodiment of the present invention.
Figure 5:
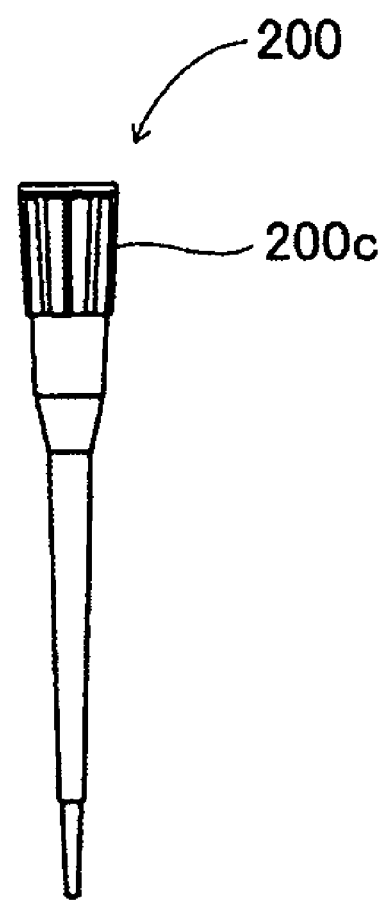
FIG. 5 is a front elevation view of a pipette tip to be installed on a sample dispensing arm in the embodiment of the present invention.

As shown in FIGS. 1 and 2, the immunoanalyzer 1 is provided with a measuring device 2 a sample conveyance section (sampler) 3 arranged on the front side of the measuring device 2, and a control device 4 which is configured by a PC (personal computer) that is electrically connected to the measuring device 2. The measuring device 2 is configured by a pipette tip supplier 30, an urgent sample/tip conveyor 20, a sample dispensing arm 5, nozzle wiping section 16, reagent placing sections 6 and 7, reagent dispensing arms 8, 9, and 10, primary reaction section 11 and secondary reaction section 12, cuvette supplier 13, BF separator 14, and detecting section 15. As shown in FIG. 2, each device (each type of dispensing arm and reagent placing section 7 and the like) in the measuring device 2 is controlled by a controller 2a provided in the measuring device 2. The sample conveyor 3 is also controlled by the controller 2a. In the immunoanalyzer 1 of the present embodiment, a disposable tip 200 (refer to FIG. 5) is replaced whenever a sample is aspirated and discharged in order to prevent a sample such as a blood sample or the like which has been aspirated and discharged by the sample dispensing arm 5 from being mixed with another sample. The various sections of the measuring device 2 are described later.

Figure 3:
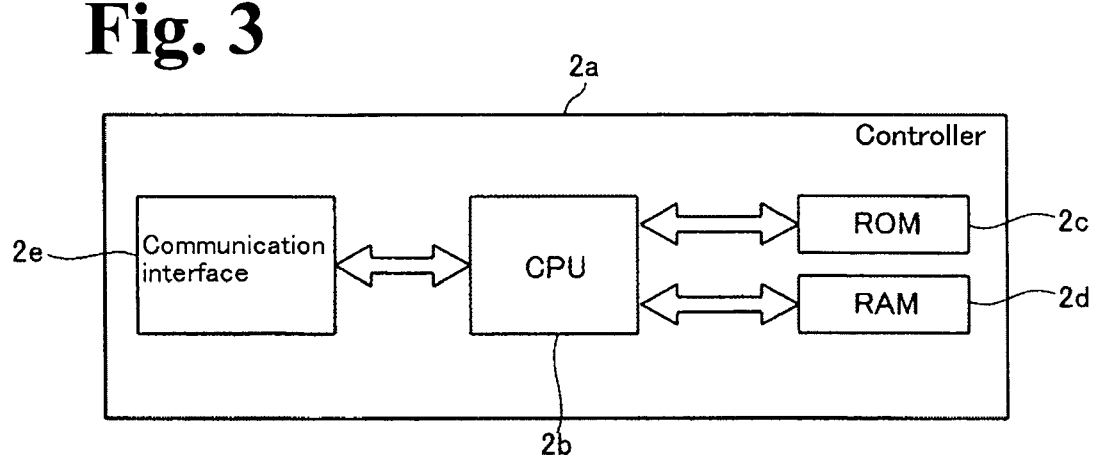
FIG. 3 is a block diagram showing the structure of the control section of the measuring device shown in FIG. 2.

As shown in FIG. 3, the controller 2a is mainly configured by a CPU 2b, ROM 2c, RAM 2d, and communication interface 2e.

The CPU 2b is capable of executing computer programs which are stored in the ROM 2c, and computer programs which are read from the RAM 2d. The ROM 2c stores computer programs which are executed by the CPU 2b, as well as the data and the like which are used in the execution of the computer programs. The RAM 2d is used when reading the computer programs stored in the ROM 2c. The RAM 2d is also used as a work area of the CPU 2b when the computer programs are being executed.

The communication interface 2e is connected to the control device 4 and has the functions of transmitting the optical information of a sample (data of the amount of light emission generated by the reaction of the labeling antibody and the luminous substrate) to the control device 4 and receiving signals from a controller 4a of the control device 4. The communication interface 2e has the function of transmitting instructions from the CPU 2b to drive the various parts of the sample conveyor 3 and the measuring device 2.

As shown in FIG. 1, the sample conveyor 3 is configured to transport a rack 101, which accommodates a plurality of test tubes 100 containing samples, to a position corresponding to an aspirating position 1a at which the sample dispensing arm 5 aspirates the sample. The sample conveyor 3 has a rack placement area 3a for placing the racks 101 which accommodate the test tubes 100 that contain unprocessed samples, and a rack storing area 3b for storing the racks 101 which accommodate the test tubes 100 that contain dispensed samples. A test tube 100 containing an unprocessed sample is then conveyed to a position corresponding to the aspirating position 1a of the sample dispensing arm 5, the sample such as blood or the like within a test tube 100 is aspirated by the sample dispensing arm 5, and the rack 101 which accommodates this test tube 100 is thereafter stored in the rack storing area 3b. A barcode which records the identification information that identifies the contained sample is adhered to each test tube 100. The test tubes 100 which are accommodated in the racks 101 placed in the rack placing area 3a are transported to the aspirating position 1a after the identification information of each has been read by a barcode reader that is not shown in the drawing.

The control device 4 (refer to FIG. 1) is configured by a personal computer (PC) which includes a controller 4a configured by a CPU, ROM, RAM and the like, a display unit 4b, and a keyboard 4c. The display unit 4b is provided to display analysis results and the like obtained by analyzing digital signal data transmitted from the detecting section 15. The structure of the control device 4 is described below.

Figure 4:
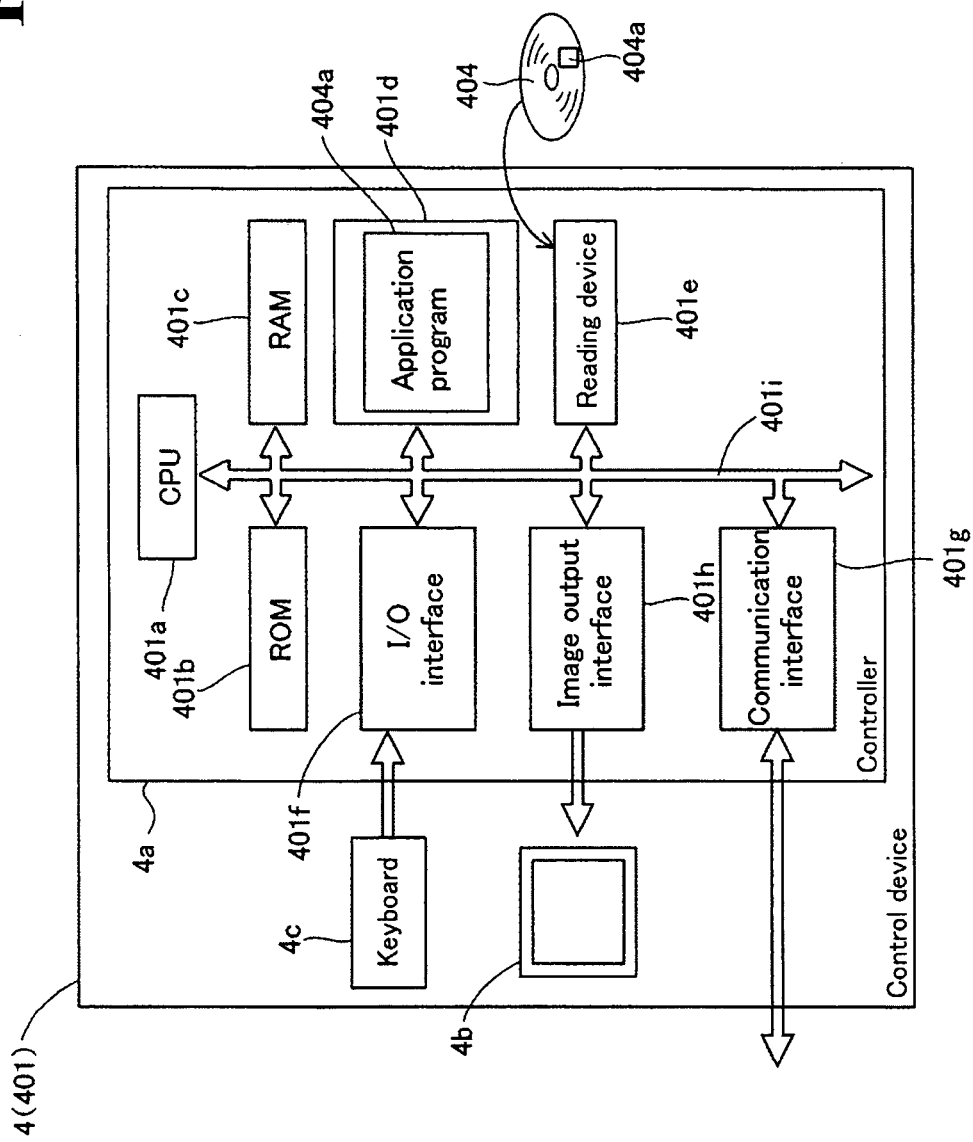
FIG. 4 is a block diagram showing the control device of the immunoanalyzer of the embodiment of the present invention.

The control device 4 is a computer 401 mainly configured by a controller 4a, display unit 4b, and keyboard 4c, as shown in FIG. 4. The controller 4a is mainly configured by a CPU 401a, ROM 401b, RAM 401c, hard disk 401d, reading device 401e, input/output (I/O) device 401f, communication interface 401g, and image output interface 401h. The CPU 401a, ROM 401b, RAM 401c, hard disk 401d, reading device 401e, I/O interface 401f, communication interface 401g, and image output interface 401h are connected by a bus 401i.

The CPU 401a is capable of executing computer programs stored in the ROM 401b, and computer programs loaded in the RAM 401c. The computer 401 functions as the control device 4 when the CPU 401a executes an application program 404a which is described later.

The ROM 401b is configured by a mask ROM, PROM, EPROM, EEPROM or the like, and stores computer programs executed by the CPU 401a and data and the like used in conjunction therewith.

The RAM 401c is configured by SRAM, DRAM or the like. The RAM 401c is used when reading the computer program recorded in the ROM 401b and on the hard disk 401d. The RAM 401c is also used as a work area of the CPU 401a when the computer program is being executed.

The hard disk 401d contains various installed computer programs to be executed by the CPU 401a such as an operating system and application program 404a and the like, as well as data used in the execution of these computer programs. The application program 404a used for immunoanalysis in the present embodiment is also installed on the hard disk 401d. The CPU 401a obtains the amount of antigen in a measurement sample based on the amount of light emission (digital signal data) of the measurement sample transmitted from the detecting section 15 of the measuring device 2 by executing the application program 404a. An operating system which provides a graphical user interface, such as Windows (registered trademark) or the like, a product of Microsoft Corporation, USA, is installed on the hard disk 401d. The application program 404a operates on this operating system.

The reading device 401e is configured by a floppy disk drive, CD-ROM drive, DVD-ROM drive or the like, and is capable of reading the computer programs and data stored on a portable recording medium 404. The portable recording medium 404 stores the immunoanalysis application program 404a, and the application 404a is read from the portable recording medium 404 by the computer 401, which installs the application program 404a on the hard disk 401d.

The application program 404a is not only provided the portable recording medium 404 inasmuch as the application program 404a may also be provided from an external device which is connected to the computer 401 over an electric communication line so as to be capable of communication by this electric communication line (whether wire line or wireless). For example, when the application program 404a is stored on the hard disk of a server computer on the Internet, the computer 401 accesses the server computer and downloads the application program 404a, which is then installed on the hard disk 401d.

The I/O interface 401f is configured, for example, by a serial interface such as a USB, IEEE1394, RS232C or the like, a parallel interface such as SCSI, IDE, IEEE1284 or the like, and an analog interface such as a D/A converter, A/D converter or the like. The keyboard 4c is connected to the I/O interface 401f, so that a user can input data in the computer 401 using the keyboard 4c.

The communication interface 401g is, for example, an Ethernet (registered trademark) interface. The computer 401 can send and receive data to and from the measuring device 2 via the communication interface 401g using a predetermined communication protocol.

The image output interface 401h is connected to the display unit 4b which is configured by an LCD, CRT or the like, so that image signals corresponding to the image data received from the CPU 401a can be output to the display unit 4b. The display unit 4b displays images (screens) in accordance with the input image signals.

The sections of the measuring device 2 are described below. The pipette tip supplier 30 (refer to FIG. 1) has the function of supplying the large quantity of pipette tips 200, which are stored in a tip hopper (not shown in the drawing), one by one to the urgent sample/tip conveyor 20. The urgent sample/tip conveyor 20 is configured to interrupt a sample being conveyed by the sample conveyor 3 to convey a test tube 102, which contains a sample requiring urgent examination, to an installation position 1b (refer to FIG. 1) where a pipette tip 200 is installed on the sample dispensing arm 5. The urgent sample/tip conveyor 20 is also configured to convey a pipette tip 200, which has been received from the pipette tip supplier 30, to the installation position 1b of the sample disopensing arm 5.

Figure 6:
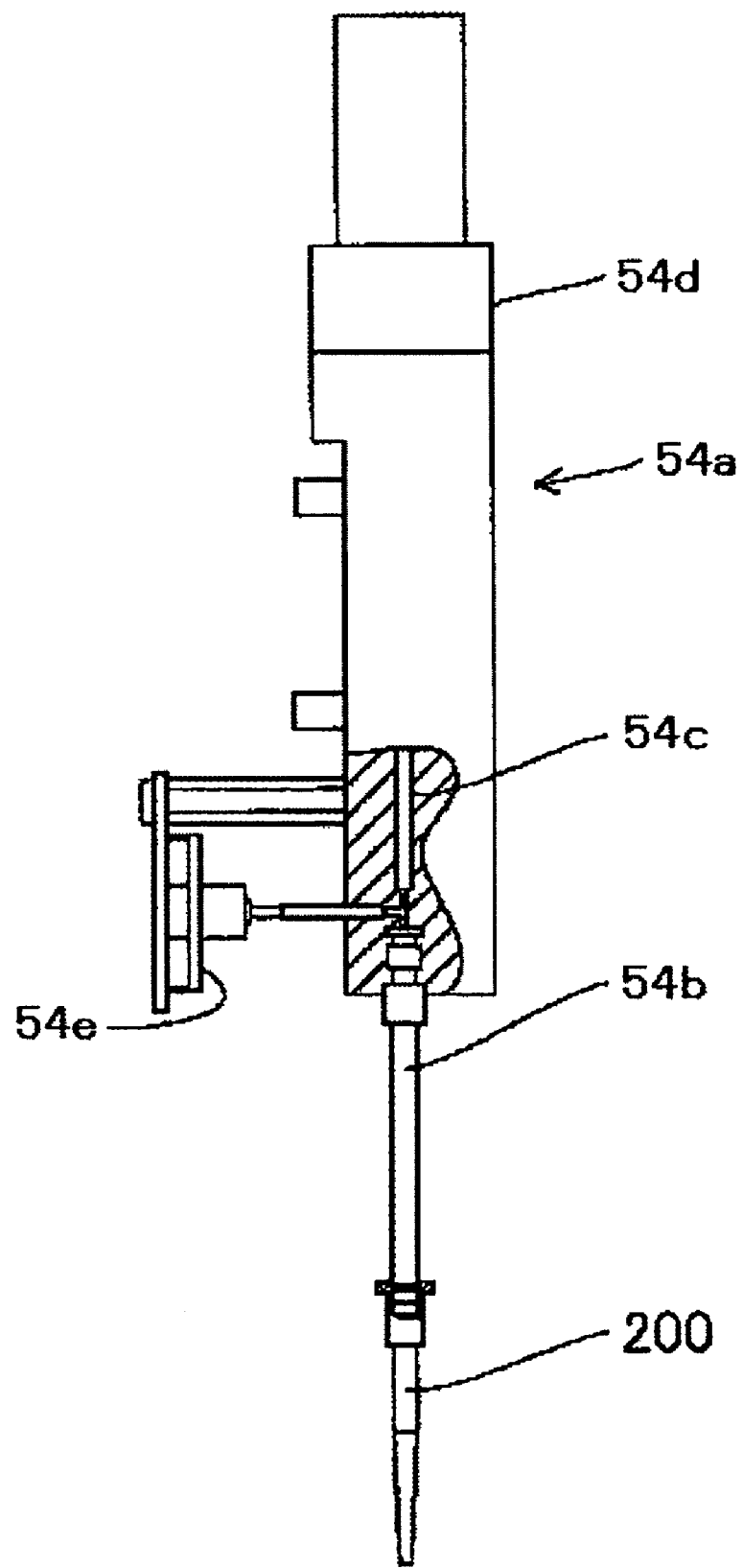
FIG. 6 is a brief illustration of the structure of the nozzle part and syringe part in the sample dispensing arm in the embodiment of the present invention.
Figure 12:
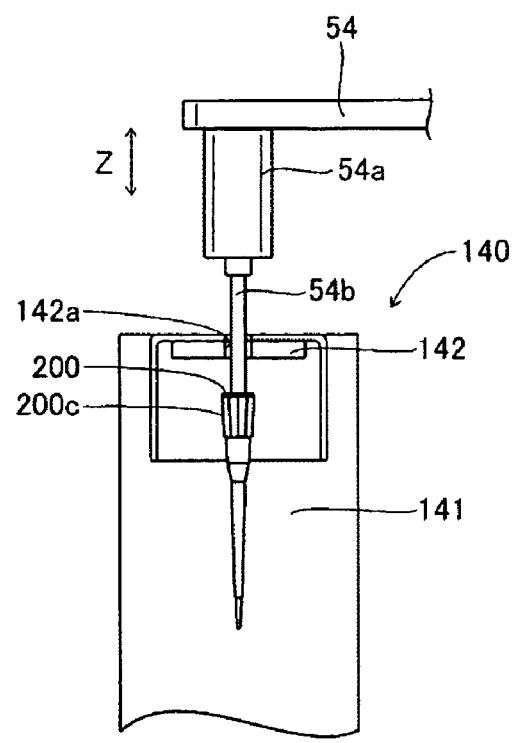
FIG. 12 is a side view illustrating the operation for detaching the pipette tip installed on the sample dispensing arm of the immunoanalyzer shown in FIG. 1.

The sample dispensing arm 5 has the function of dispensing a sample within a test tube 100 that has been conveyed to the aspirating position 1a (refer to FIG. 1) by the sample conveyor 3, or a sample within a test tube 102 that has been transported to the installing position 1b (refer to FIG. 1) by the urgent sample/tip conveyor 20, into a cuvette 150 that is held by a holder 11b of a rotating table 11a of the primary reaction section 11 which is described later. As shown in FIG. 1, the sample dispensing arm 5 is provided with a motor 51, a drive transmission unit 52 which is connected to the motor 51, an arm 54 which is mounted on the drive transmission unit 52 via a shaft 53, an arm support 55 for supporting the arm 54, and a horizontal drive device 56 which is capable of moving the arm support 55 in horizontal directions. The drive transmission unit 52 is configured to rotate the arm 54 pivoting on the shaft 53 using the drive force from the motor 51, and move the arm 54 in vertical directions (Z direction). As shown in FIGS. 6 and 12, the arm 54 is provided with a syringe part 54a, and a nozzle part 54b. The syringe part 54a is provided with a pump unit 54c for aspirating and discharging a sample, a motor 54d which is the drive source of the pump unit 54c, and a pressure sensor 54e. The aspiration and discharge functions of the pump unit 54c are obtained by converting the rotation of the motor 54d to a piston movement. The pressure sensor 54e detects the pressure during aspiration and discharge by the pump unit 54c.

Figure 8:
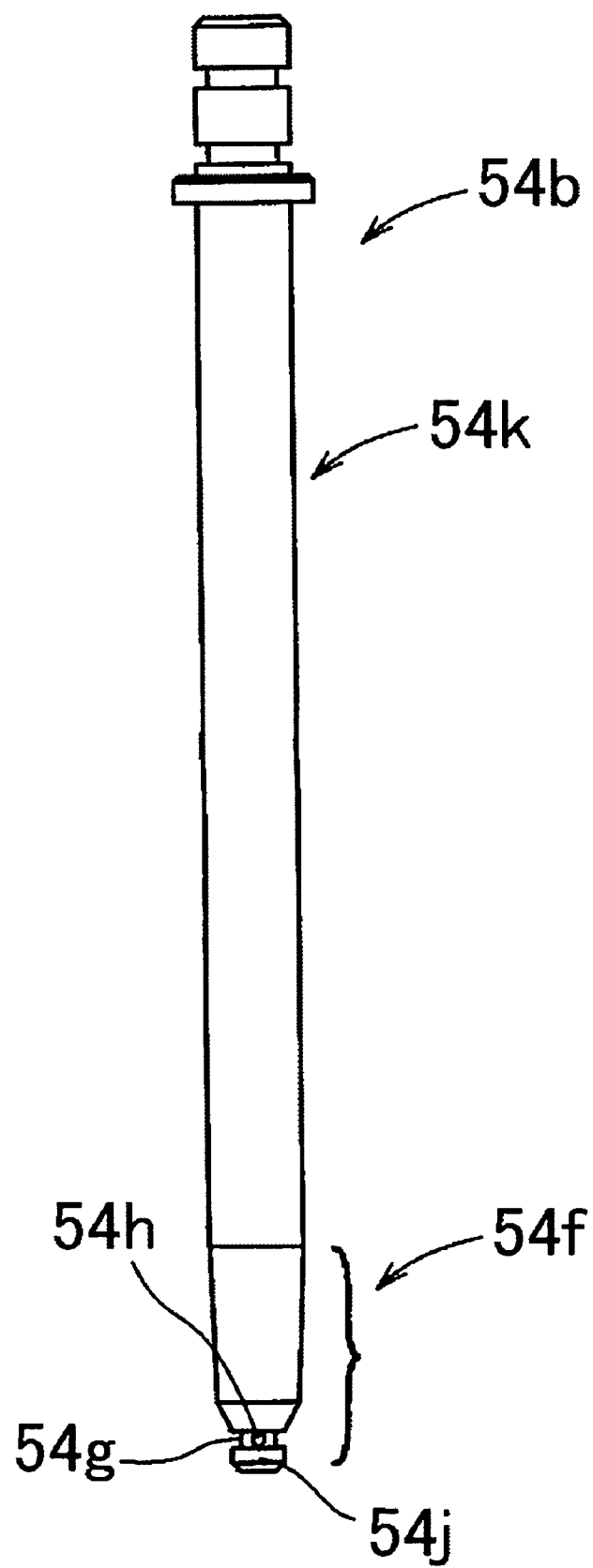
FIG. 8 is a front elevation view of the nozzle part provided in the sample dispensing arm of the embodiment of the present invention.
Figure 9:
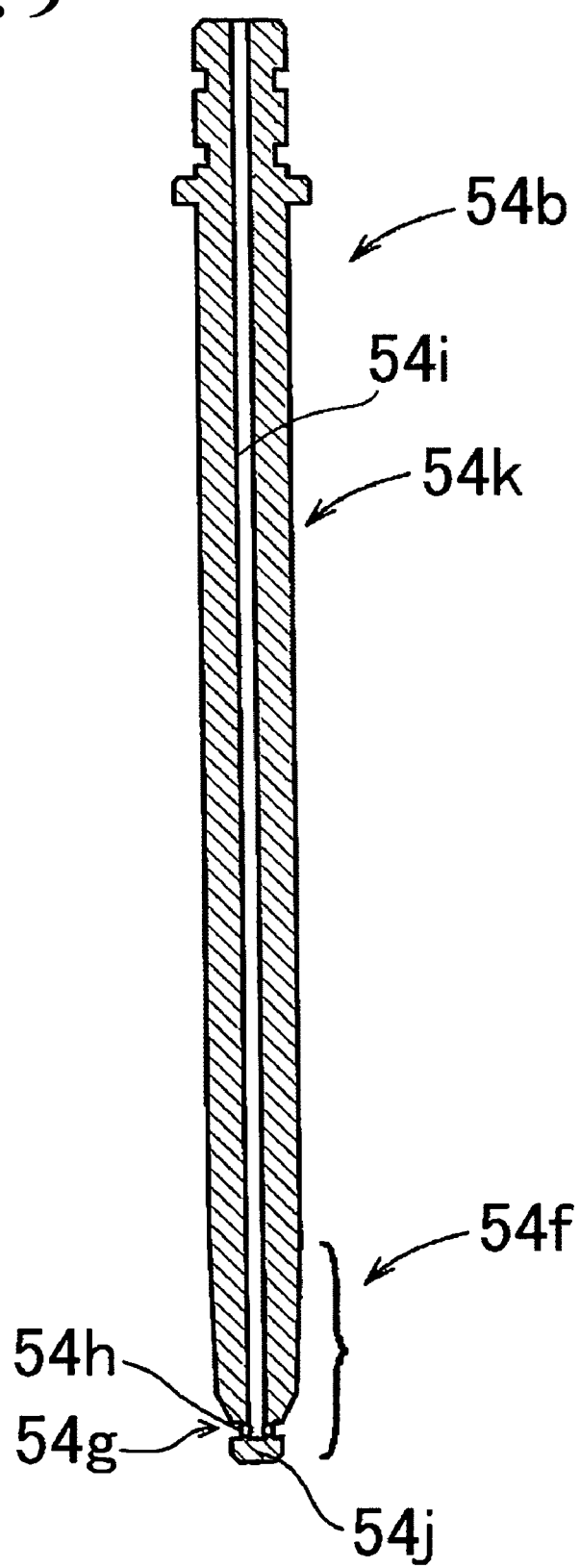
FIG. 9 is a vertical cross section view of the nozzle part of FIG. 8.

As shown in FIGS. 8 and 9, the nozzle part 54b is provided with a nozzle body 54k and a tip 54f, and an aspiration flow path 54i is formed on the center axis of the nozzle part 54b within the interior of the nozzle part 54b. The nozzle body 54k and tip 54f have a circular cross section in the horizontal direction. A pipette tip 200, which has been conveyed by a transport rack 23 (refer to FIG. 1) of the urgent sample/tip conveyor 20, is installed on the tip 54f. The tip 54f of the nozzle part 54b has a constricted part 54g of an approximately cylindrical shape and an external diameter that is narrower than the diameter above and below, and a terminus 54j of an approximately cylindrical shape and an external diameter that is larger than the external diameter of the constricted part 54g. The side surfaces of the constricted part 54g is provided with two aspirating holes 54h so as to open laterally for aspirating a sample within the pipette tip 200 which is mounted on the tip 54f of the nozzle part 54b. The aspirating holes 54h are connected to the pump unit 54c through the aspirating path 54i in the interior of the nozzle part 54b. The two aspirating holes 54h are provided in an approximately linear configuration in the constricted part 54g through the aspirating path 54i. That is, the aspirating holes 54h are provided so that the aspirating path 54i and the two aspirating holes 54h form an approximate inverted T configuration in the vertical cross section in the tip 54f, as shown in FIG. 9. The bottom surface of the terminus 54j is flat.

Figure 10:
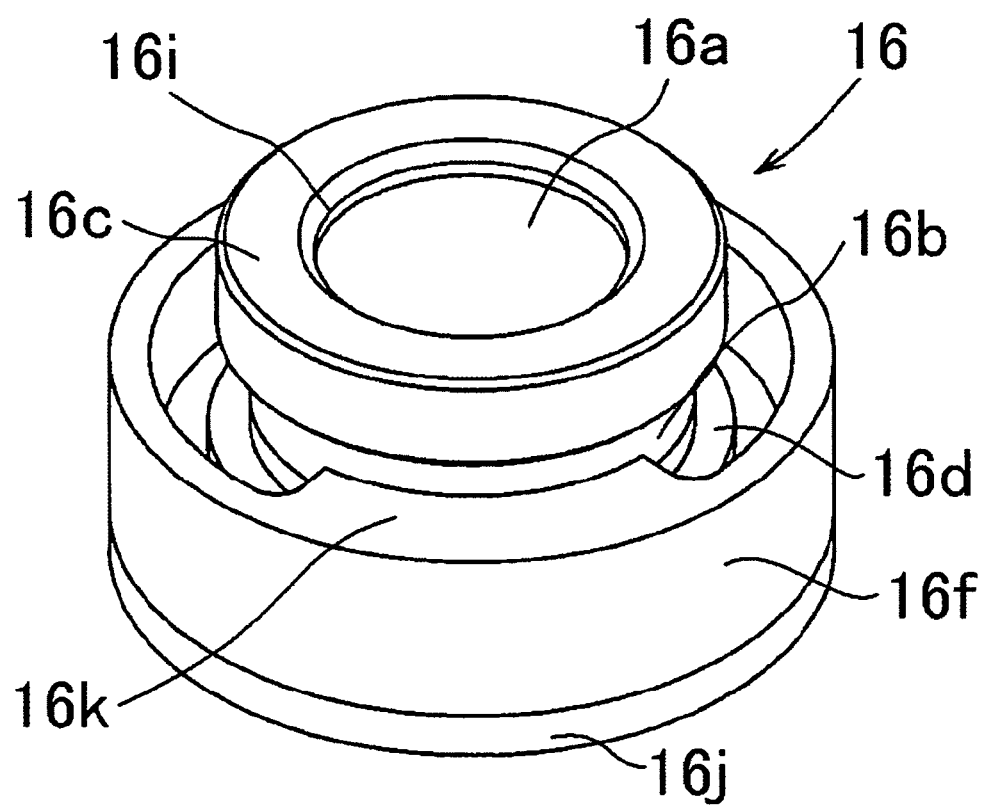
FIG. 10 is a perspective view of the nozzle wiping section in the embodiment of the present invention.
Figure 11:
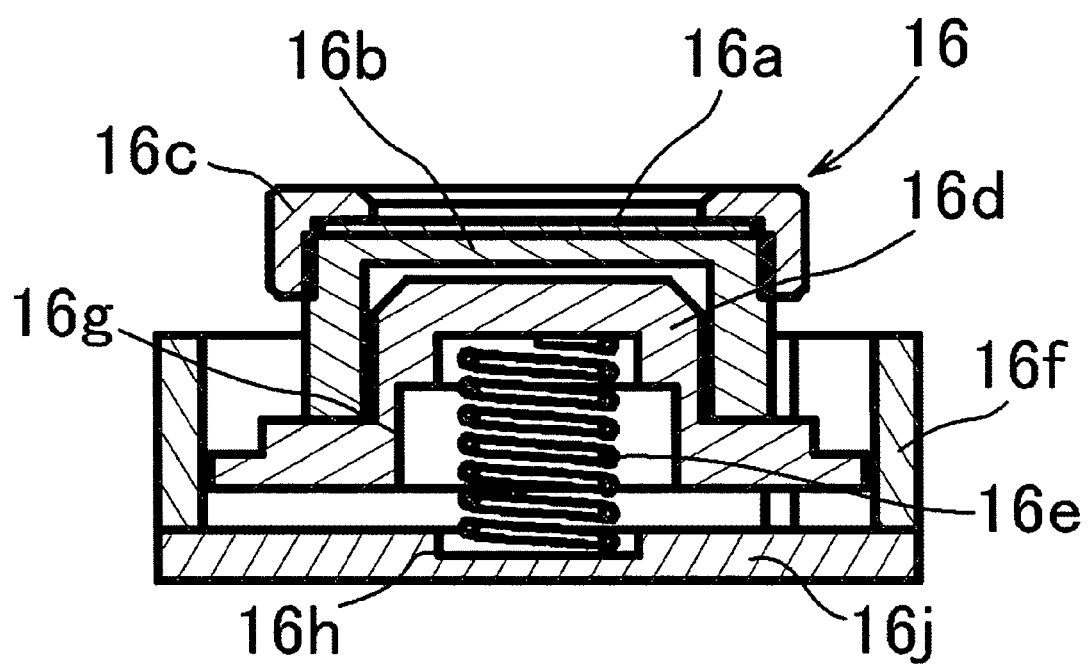
FIG. 11 is a vertical cross section view of the nozzle wiping section of FIG. 10.

The nozzle wiping section 16 (refer to FIGS. 1, 10, and 11) has the function of wiping the adhered sample (resulting from the sample dispensing operation) from the bottom surface of the terminus 54j of the tip 54f of the nozzle part 54b on the sample dispensing arm 5. As shown in FIGS. 10 and 11, the nozzle wiping section 16 is provided with a filter paper 16a, a mounting member 16b for mounting the filter paper 16a, an aperture 16i, a anchoring member 16c for anchoring the mounting member 16b on which the filter paper 16a is mounted, a supporting member 16d for supporting the mounting member 16b, a spring 16e, external wall member 16f, and bottom member 16j. The mounting member 16b, supporting member 16d, and spring 16e are accommodated in a space formed by the bottom member 16j and the exterior wall member 16f. The bottom member 16j is mounted on the exterior wall member 16f by a screw (not shown in the drawing). Thread-like channels (not shown in the drawings) are formed on the interior surface of the anchoring member 16c and the exterior surface of the mounting member 16b so that the anchoring member 16c is bound to the mounting member 16b by rotation. The filter paper 16a, which is mounted on the mounting member 16b, is anchored by the anchoring member 16c by tightening the anchoring member 16c in the mounting member 16b. A concavity 16g is formed in the supporting member 16d, and a concavity 16h is formed in the top surface of the bottom member 16j. The spring 16e is accommodated in the space formed by the exterior wall 16f and the bottom member 16j so that one end of the spring 16e is inserted into the concavity 16g of the supporting member 16d, and the other end is inserted into the concavity 16h formed in the bottom member 16j. Thus, the mounting member 16b and the supporting member 16d thus receive a force exerted by the spring 16e in a direction away from the bottom member 16j. The movement of the mounting member 16b and the supporting member 16d resulting from the force exerted by the spring 16e is restricted by a convexity (not shown in the drawings) of the mounting member 16b abutting a convexity 16k of the exterior wall member 16f.

A tip separating section 140 (refer to FIGS. 1 and 12) is provided to detach the pipette tip 200 installed on the sample dispensing arm 5. As shown in FIG. 12, the tip separating section 140 is provided with a metal plate 141 disposed so as to extend in a vertical direction (Z direction), a release fixture 142 which is mounted on the metal plate 141, and a tip container (not shown in the drawing) which accommodates the detached pipette tips 200. The release fixture is configured by a hole 142a which has a diameter that is smaller than the diameter of the mounting part 200c (refer to FIG. 5) of the pipette tip 200 and larger than the diameter of the tip 54f (refer to FIG. 14) of the arm 54 on the sample dispensing arm 5, and a hole 142b into which the nozzle part 54b, on which the pipette tip 200 is mounted, is inserted from above.

The reagent placing section 6 (refer to FIG. 1) is provided to accommodate a reagent bin that holds R1 reagent which includes a capture antibody, and a reagent bin that holds R3 reagent that includes labeling antibody.

The reagent placing section 7 is provided to accommodate a reagent bin that holds R2 reagent that includes magnetic particles.

The cuvette supplier 13 (refer to FIG. 1) is configured so as to be capable of sequentially supplying a plurality of cuvettes 150 to a hold 11b of the rotating table 11a in the primary reaction section 11.

The primary reaction section 11 (refer to FIG. 1) is provided to rotationally move the cuvettes 150, which are held by the holder 11b of the rotating table 11a, at a predetermined angle at predetermined intervals, and mix the sample, R1 reagent and R2 reagent within the cuvette 150. The primary reaction section 11 is provided with a sample conveyor 11c for conveying a cuvette 150, which contains R1 reagent and R2 reagent, to the BF separator 14 which is described later.

The reagent dispensing arm 8 (refer to FIG. 1) has the functions of aspirating the R1 reagent within the reagent bin disposed in the reagent placing section 6, and dispensing the aspirated R1 reagent into a cuvette 150, which contains the previously dispensed sample of the holder 11b of the rotating table 11a inn the primary reaction section 11.

The reagent dispensing arm 9 (refer to FIG. 1) has the function of dispensing the R2 reagent, contained in the reagent bin disposed in the reagent placing section 7, into the cuvette 150, which contains the previously dispensed R1 reagent and sample of the primary reaction section 11.

The BF separator 14 has the function of separating the magnetic particles and free R1 reagent (unnecessary component) from the sample within the cuvette 150 which has been conveyed by the container conveyor 11c of the primary reaction section 11, and has the function of separating the magnetic particles and the free R3 reagent (unnecessary component) from the sample within the cuvette 150 which has been conveyed by a container conveyor 12c of the secondary reaction section 12. The cuvette 150 from which the free R1 reagent and the like has been separated by the BF separator 14 is then conveyed to a holder 12b of the rotating table 12a in the secondary reaction section 12 by a catcher unit (not shown in the drawing).

The secondary reaction section 12 (refer to FIG. 1) has a configuration identical to the primary reaction section 11, and is provided to rotationally move the cuvette 150 in the holder 12b of the rotating table 12a by a predetermined angle at predetermined intervals, and mix the sample, R1 reagent, R2 reagent, R3 reagent, and R5 reagent contained in the cuvette 150. The secondary reaction section 12 has a sample conveyor 12c for conveying a cuvette, which contains mixed sample and the like, to the BF separator 14. The sample conveyor 12c has the function of reconveying the cuvette 150, which has been processed by the BF separator 14, to the holder 12b of the rotating table 12a.

The reagent dispensing arm 10 (refer to FIG. 1) has the function of aspirating the R3 reagent contained in the reagent bin disposed in the reaction section 6, and the function of dispensing the aspirated R3 reagent into the cuvette 150 which contained the dispensed sample, R1 reagent and R2 reagent of the primary reaction section 11. The reagent dispensing arm 10 also has the function of dispensing R5 reagent, which includes a luminous substrate within a reagent bin (not shown in the drawing) disposed in the bottom part of the immunoanalyzer 1, into the cuvette 150 which contains the sample, R1, reagent, R2 reagent, and R3 reagent of the secondary reaction section 12.

The detecting section 15 (refer to FIG. 1) is provided to measure the amount of antigen contained in the sample by using a photomultiplier tube to detect the light generated by the reaction process of the luminous substrate and labeling antibody bound to the antigen in the sample which has been subjected to predetermined processing.

Figure 7:
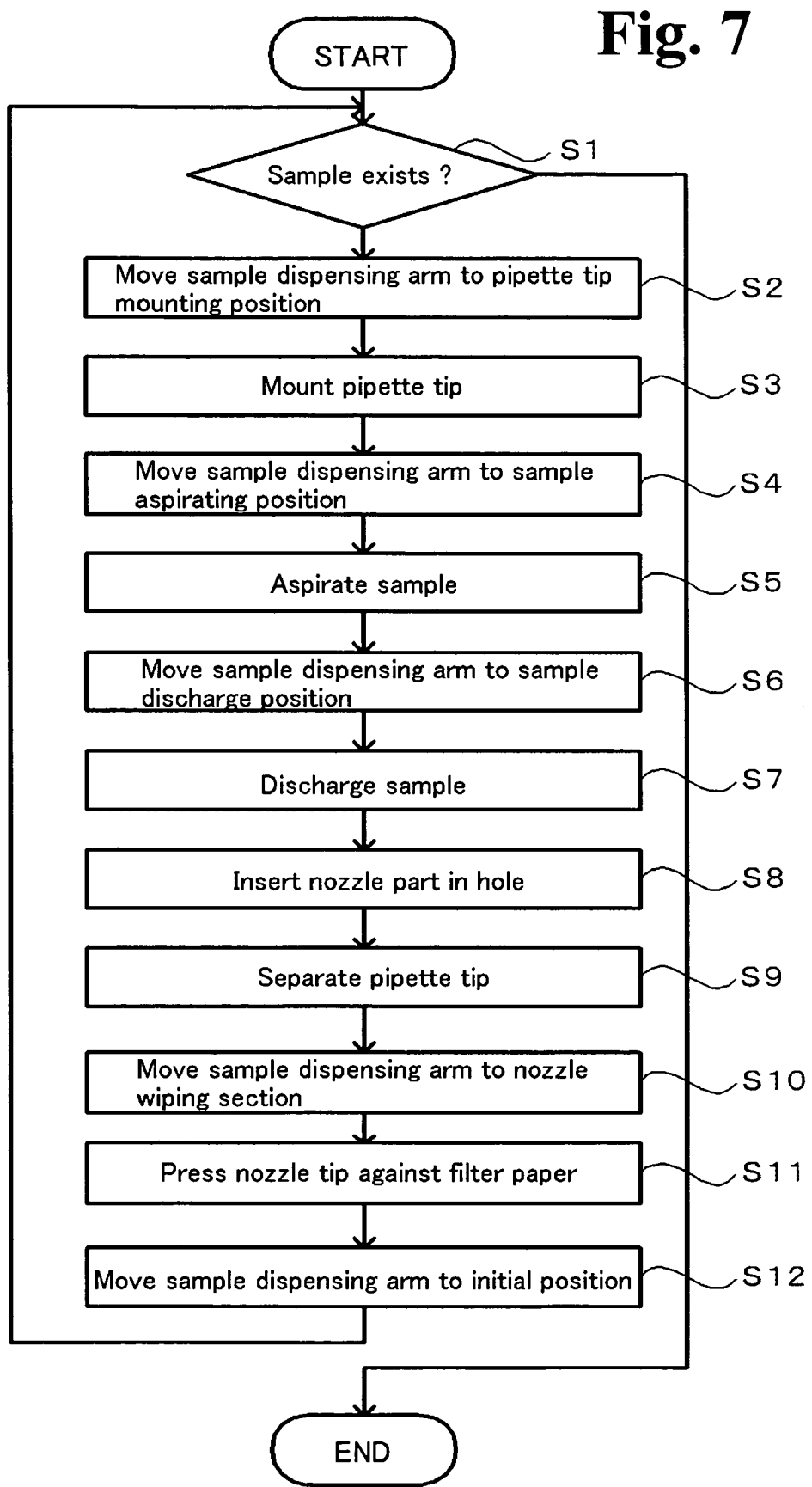
FIG. 7 is a flow chart of the sample dispensing process performed by the control section of the measuring device using the sample dispensing arm in the embodiment of the present invention.

The sample dispensing process performed by the controller 2a of the measuring device 2 using the sample dispensing arm 5 is described below with reference to the flow chart of FIG. 7.

When executing the sample dispensing process, the controller 2a requests order information from the controller 4a of the control device 4 based on the identification information of the test tube 100 read by the barcode reader, and receives the order information from the controller 4a. The order information is recorded in a host computer (not shown in the drawings) of the control device 4, and is stored when the information is input to the control device 4 by a user. The controller 2a determines whether or not a sample is a dispensing object based on the order information received from the controller 4a (step S1). When the sample is not a dispensing object, the controller 2a does not perform the sample dispensing process.

When the power source (not shown in the drawing) of the measuring device 2 is turned ON by a user operation, the nozzle part 54b of the arm 54 on the sample dispensing arm 5 is moved to an initial position above the tip separating section 140 by the controller 2a initializing the sample dispensing arm 5. Then, when the controller 2a determines that the sample is a dispensing object in the process of step S1, the urgent sample/tip conveyor 20 is controlled to convey a pipette tip 200 to the installing position 1b, and the nozzle part 54b of the arm 5d is moved from the initial position above the tip separating section 140 to the installing position 1b (step S2). The controller 2a then lowers the arm 5d and press fits the tip 54f of the nozzle part 54b into the mounting part 200c of the pipette tip 200 to install the pipette tip 200 on the nozzle part 54b of the arm 54d (step S3).

Then, the controller 2a raises the nozzle part 54b of the arm 54 on the sample dispensing arm 5, and thereafter moves the nozzle part 54b of the arm 54 to the aspirating position (refer to FIG. 1) where samples are aspirated (step S4). The controller 2a then lowers the arm 54, and subsequently controls the arm 54 to aspirate the sample contained in a test tube 100, which has been conveyed to the aspirating position 1a by the sample conveyor 3, into the pipette tip 200 mounted on the tip 54f of the nozzle part 54b (step S5).

Thereafter, the controller 2a raises the arm 54 and then moves the nozzle part 54b of the arm 54 to a position above the holder 11b of the rotating table 11a in the primary reaction section 11 (step S6). The controller 2a then lowers the arm 54 and discharges the sample into the cuvette 150 which is held by the holder 1b of the rotating table 1a in the primary reaction section 11 (step S7).

Figure 13:
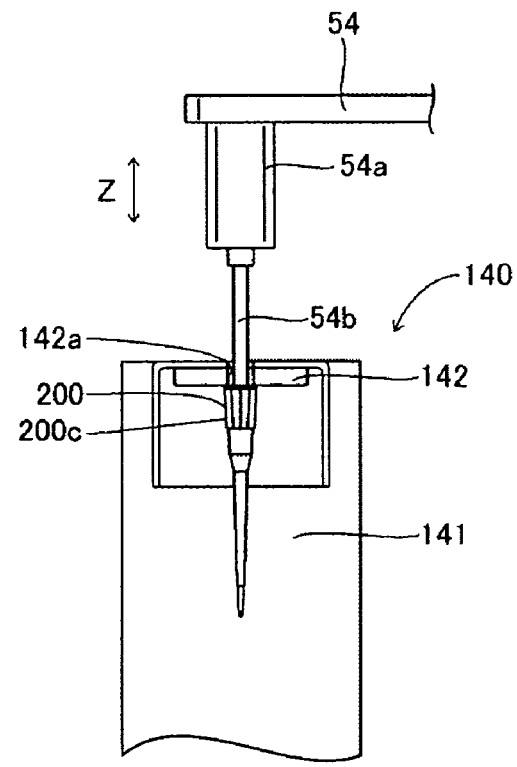
FIG. 13 is a side view illustrating the operation for detaching the pipette tip installed on the sample dispensing arm of the immunoanalyzer shown in FIG. 1.
Figure 14:
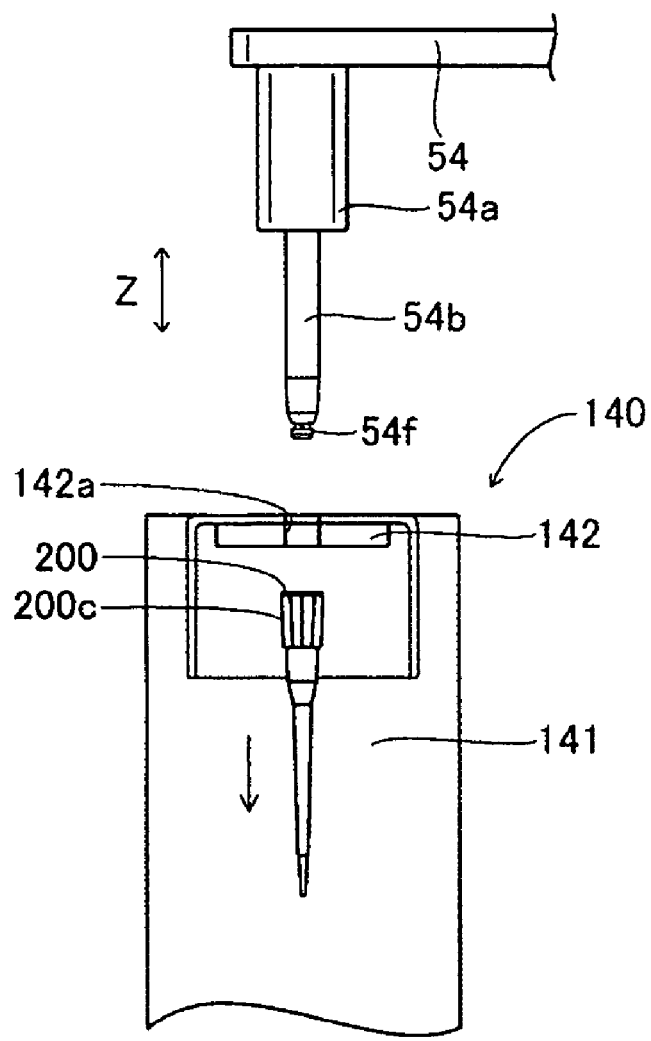
FIG. 14 is a side view illustrating the operation for detaching the pipette tip installed on the sample dispensing arm of the immunoanalyzer shown in FIG. 1.

Next, the controller 2a raises the arm 54 and thereafter moves the nozzle part 54b to a position above the hold 142b of the release fixture 142 in the tip separating section 140. The controller 2a subsequently lowers the arm 54 and inserts the nozzle part 54b, on which the used pipette tip 200 is installed, into the hole 142b of the tip separating section 140 (step S8). The nozzle part 54b, which is inserted into the hole 142b, is controlled so as to move downward in the hole 142a at the separating position via a horizontal movement as shown in FIG. 12. Thereafter, the nozzle part 54b is raised via control by the controller 2a. The top surface of the mounting part 200c of the pipette tip 200 therefore comes into contact with the bottom surface of the releasing fixture 142 in conjunction with the raising operation of the nozzle part 54b, as shown in FIG. 13. The pipette tip 200 is then separated from the tip 54f of the nozzle part 54b, as shown in FIG. 14 (step S9).

The controller 2a then moves the nozzle part 54b of the arm 54 above the nozzle wiping section 16 (refer to FIG. 1 (step S10). The controller 2a subsequently lowers the arm 54 and presses the terminus 54j of the tip 54f of the nozzle part 54b against the filter paper 16a of the nozzle wiping section 16 (step S11).

The controller 2a then raises the arm 54 and moves the nozzle part 54b of the sample dispensing arm 5 to the initial position above the tip separating section 140 (step S12). After the process of step S12, the controller 2a again executes the process of step S1.

The above description pertains to an example concerning the aspiration of a sample in a test tube 100 conveyed by the sample conveyor 3; when examining an urgent sample, however, the controller 2a rotates the nozzle part 54b of the arm 54f on the sample dispensing arm 5 to the mounting position 1b (refer to FIG. 1) in the process of step S4. The controller 2a then controls the arm 54 in the process of step S5 to aspirate a sample contained in a test tube 100, which has been conveyed to the mounting position 1b by the urgent sample/tip conveyor 20, into the pipette tip 200 installed on the tip 54f of the nozzle part 54b.

Furthermore, in the process of step S9, there is concern that residual sample in the pipette tip 200 may be scattered by the impact when separating the used pipette tip 200 from the tip 54f of the nozzle part 54b causing the sample to adhere to the bottom surface of the terminus 54j at the tip 54f of the nozzle part 54b. In the present embodiment, the sample adhered to the bottom surface of the terminus 54j can be wiped since the terminus 54j of the tip 54f of the nozzle part 54b is pressed against the filter paper 16a in the process of step S11. Therefore, previously used sample is reliably prevented from contaminating the next sample, and reliability of measurement accuracy is improved.

In the present embodiment, the aspirating hole 54h for aspirating sample is provided as an lateral facing opening at the tip 54f of the nozzle part 54b. Therefore, the sample is prevented from adhering to the interior of the aspirating hole 54h since the sample scatters downward from the nozzle part 54b even if residual sample in the pipette tip 200 is scattered when separating the pipette tip. Accordingly, sample adhered to the interior of the aspirating hole 54h is prevented from contaminating another sample used in a subsequent analysis, and an operation error by the pressure sensor 54, which detects the pressure within the nozzle part 54b, is also prevented.

In the present embodiment, sample is reliably prevented from adhering to the interior of the aspirating holes 54h by providing the aspirating hole 54h in the constricted part 54g which has an external diameter narrower than the diameter above and below.

In the present embodiment, sample is reliably prevented from adhering to the aspirating hole 54h by providing the approximately cylindrical terminus 54j, which has an external diameter larger than the external diameter of the constricted part 54g, below the constricted part 54g which his provided with the aspirating hole 54h.

In the present embodiment, the bottom surface of the terminus 54j of the tip 54f at the nozzle part 54b is flat. In the process of step S11, therefore, the entire bottom surface of the terminus 54j is uniformly pressed against the filter paper 16a when the terminus 54j at the tip 544 of the nozzle part 54b is pressed against the filter paper 16a of the nozzle wiping section 16. The sample adhered to the bottom surface of the terminus 54j is thus easily wiped off. The bottom surface of the terminus 54j can be easily cleaned by forming a flat surface on the bottom surface of the terminus 54j even when using a cleaning means other than the nozzle wiping section 16.

Figure 15:
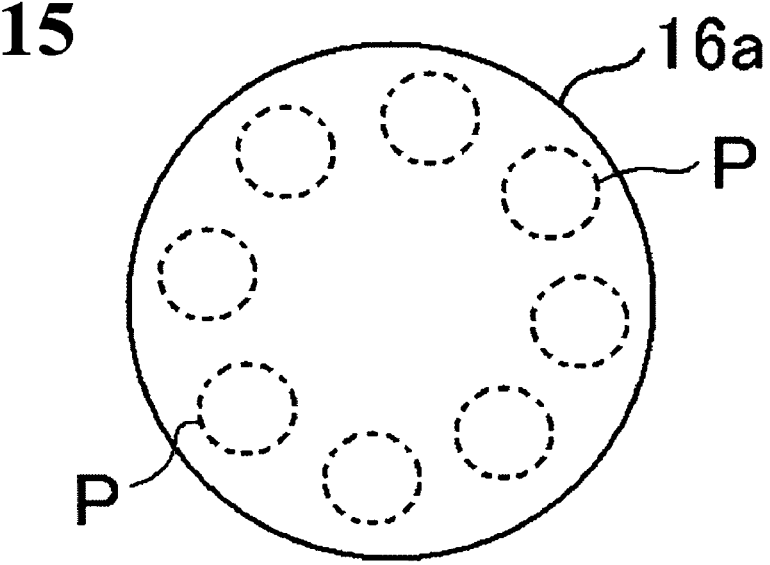
FIG. 15 shows the position at which the nozzle of the sample dispensing arm of the immunoanalyzer of FIG. 1 is pressed against the filter paper of the nozzle wiping section of FIG. 10.

In the present embodiment, the controller 2a controls the movement of the sample dispensing arm 5 so as to change the position at which the terminus 54j of the nozzle part 54b presses against the filter paper 16a of the nozzle wiping section 16 in the processes of steps S10 and S11. Specifically, the controller 2a controls the movement of the sample dispensing arm 5 so that the respective pressing positions (P) of the terminus 54j of the nozzle part 54b on the filter paper 16a traces a circle, as shown in FIG. 15. Therefore, the nozzle part 54b is prevented from being recontaminated by a sample adhered to the filter paper 16a, the use time of the filter paper 16a is increased, and frequency of replacing the filter paper 16a is reduced.

In the present embodiment, the nozzle wiping section 16 is provided with a spring 16e, and configured so that the spring 16e supports the support member 16d and the mounting member 16b from below. In the process of step S11, therefore, the mounting member 16b and supporting member 16d of the nozzle wiping section 16 both move downward when the filter paper 16a is pressed by the tip 54f of the nozzle part 54b. Accordingly, when the tip 54f of the nozzle part 54b is pressed against the filter paper 16a, a reduced repelling force is received by the tip 54f of the nozzle part 54b from the mounting member 16b and supporting member 16d.

Figure 16:
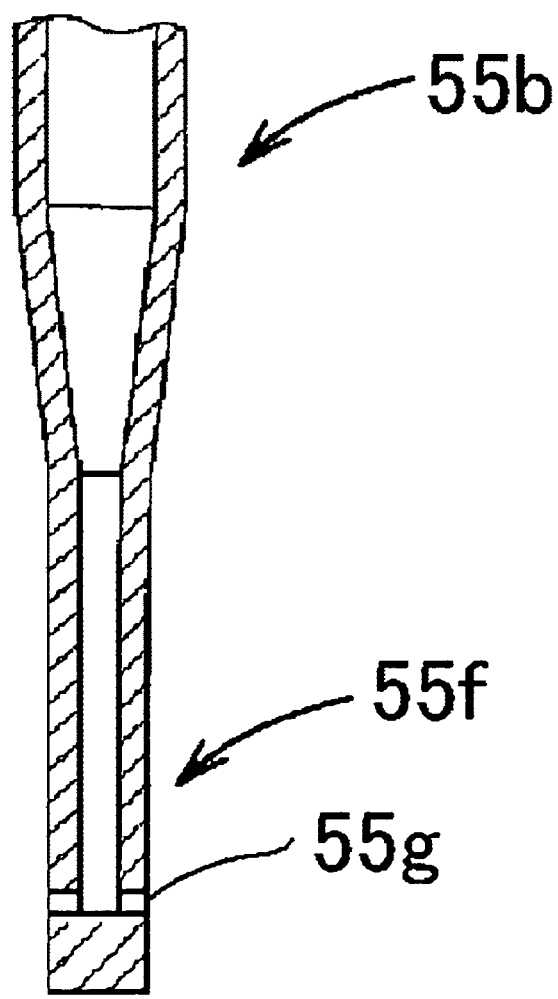
FIG. 16 is a vertical cross section view of the nozzle part of another embodiment of the present invention.
Figure 17:
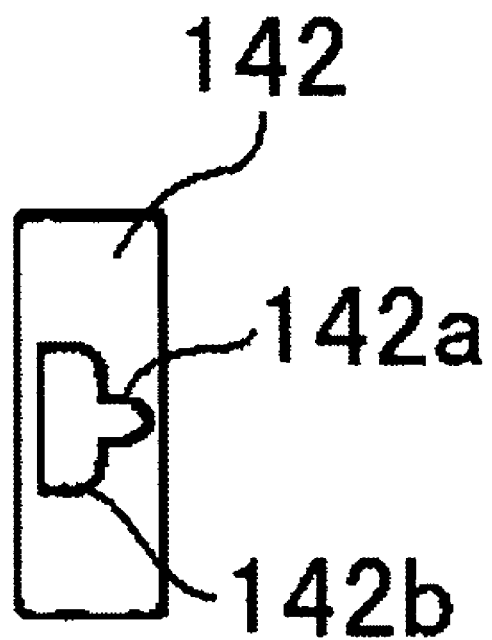
FIG. 17 is a plan view of the release fixture of the tip separating section shown in FIG. 1.

Although the aspirating hole 54h is provided in the constricted part 54g of the nozzle part 54b in the present embodiment, an aspirating hole may also be provided so as to open facing laterally near the tip of the nozzle part rather than at the constricted part 54g; for example, an aspirating hole 55g which opens facing laterally may be provided at a tip 55f that has an entirely uniform external diameter as in the nozzle part 55b shown in FIG. 16.

Although the aspirating hole 54h is provided so as to open facing laterally at the nozzle part 54b in the present embodiment, an aspirating hole may also be provided so as to open facing downward.

In the present embodiment, two aspirating holes 54h are provided at the constricted part 54g of the nozzle part 54b, however a single aspirating hole may also be provided. Moreover, three or more aspirating holes may be provided.

In the process of step S11 of the present embodiment, operation of wiping the sample adhered to the tip 54f of the nozzle part 54b is performed by moving the nozzle part 54b downward and pressing the tip 54f of the nozzle part 54b against the filter paper 16a, however, the present invention is not limited to this method. For example, a configuration is also possible in which the sample adhered to the tip of the nozzle part is wiped by brining a hygroscopic tape-like member mounted on a roller into surface contact with the tip 54f of the nozzle part 54b, and rotating the roller to wind the tape-like member. Furthermore, the sample adhered to the tip 54f of the nozzle part 54b may also be removed by cleaning the tip 54f of the nozzle part 54b using a cleaning solution stored in a container. In this case, the cleaning solution adhered to the tip 54f of the nozzle part 54b may be dried or wiped.

Although an aspirating hole 55f which opens facing laterally is provided at the tip 54f of the nozzle part 54b of the sample dispensing arm 5 is described by way of example in the present embodiment, an aspirating hole which opens facing laterally may also be provided near the tip of the nozzle part of the reagent dispensing arm.

Although the nozzle part 54b of the sample dispensing arm 5 is cleaned by the nozzle wiping section 16 in the present embodiment, a cleaning means may also be provided to clean the nozzle part of the reagent dispensing arm.

Although the nozzle wiping part 16 is provided with a spring 16e in the present embodiment, and elastic member other than a spring may also be provided.

The present embodiment is provided with a terminus 54j which has an external diameter that is larger than the external diameter of the constricted part 54g, which is provided with the aspirating holes 54h, in order to reliably prevent sample from adhering to the aspirating hole 54h, however, the present invention is not limited to this arrangement. For example, sample can be prevented from adhering to the aspirating hole by providing a member, which has an external diameter that is larger than the external diameter of the tip 54f of the nozzle part 54b, at the tip of the nozzle part 54b even when the aspirating hole is not provided in the constricted part.

What is claimed is:

1. A liquid dispensing apparatus, comprising:
    a dispenser which comprises a dispensing nozzle for aspirating and discharging liquid on which a pipette tip is attached, and a moving mechanism for moving the dispensing nozzle;
    a separating section for separating the pipette tip from the dispensing nozzle;
    a nozzle cleaning section for cleaning a distal end of the dispensing nozzle, the nozzle cleaning section including a water absorbing member that absorbs liquid adhered to the distal end of the dispensing nozzle; and
    a controller configured to control the moving mechanism so as to move the dispensing nozzle to the separating section in order to separate the pipette tip from the dispensing nozzle, and subsequently control the moving mechanism so as to move the dispensing nozzle in order to contact the distal end of the dispensing nozzle on the water absorbing member,
    wherein the controller controls the moving mechanism so as to contact the distal end of the dispensing nozzle on the water absorbing member each time a pipette tip is separated from the dispensing nozzle, such that a contacting position of the dispensing nozzle on the water absorbing member is different from a previous contacting position of the dispensing nozzle on the water absorbing member.

2. The liquid dispensing apparatus of claim 1, wherein the moving mechanism is capable of moving the dispensing nozzle in vertical direction and horizontal direction, and the controller controls the moving mechanism so as to move the dispensing nozzle above the water absorbing member and moves the dispensing nozzle downwards in order to contact the distal end of the dispensing nozzle on the water absorbing member.

3. The liquid dispensing apparatus of claim 1, wherein the controller controls the moving mechanism such that a plurality of contacting positions of the dispensing nozzle on the water absorbing member define a circle.

4. The liquid dispensing apparatus of claim 1, wherein the nozzle cleaning section comprises an elastic member for elastically supporting the water absorbing member.

5. The liquid dispensing apparatus of claim 2, wherein a lower surface of the distal end of the dispensing nozzle has a planar shape.

6. The liquid dispensing apparatus of claim 1, wherein
    the moving mechanism is capable of moving the dispensing nozzle in vertical direction and horizontal direction; and
    the separating section comprises a contact part for separating the pipette tip from the dispensing nozzle by contacting an upper surface of the pipette tip when the moving mechanism moves the dispensing nozzle upward.

7. The liquid dispensing apparatus of claim 1, wherein the dispensing nozzle comprises:
    an aspirating hole section having an aspirating hole for aspirating the liquid into the pipette tip; and
    a preventing part for preventing liquid, scattered from the pipette tip when the pipette tip is separated from the dispensing nozzle, from adhering to the aspirating hole.

8. The liquid dispensing apparatus of claim 1, wherein the dispensing nozzle comprises an aspirating hole section having an aspirating hole for aspirating the liquid into the pipette tip, near the distal end of the dispensing nozzle, the aspirating hole being open laterally.

9. The liquid dispensing apparatus of claim 8, wherein the aspirating hole section comprises a constricted part whose external diameter is smaller than that of the dispensing nozzle above and below of the constricted part; and the aspirating hole is located at the constricted part.

10. A sample measuring apparatus, comprising:
    the liquid dispensing apparatus of claim 1;
    a sample conveyer for conveying a sample container containing liquid sample to a sample aspirating position; and
    a measuring section for measuring the liquid sample contained in a reaction container; wherein
    the dispenser aspirates the liquid sample from the sample container at the sample aspirating position into the pipette tip, and discharges the aspirated liquid sample into the reaction container.

* * * * *